United States Patent [19]

Klein

[11] Patent Number: 4,491,135

[45] Date of Patent: Jan. 1, 1985

[54] SURGICAL NEEDLE HOLDER

[76] Inventor: Harvey A. Klein, 1000 E. 19th St., Brooklyn, N.Y. 11230

[21] Appl. No.: 438,796

[22] Filed: Nov. 3, 1982

[51] Int. Cl.³ .................. A61B 17/06; A61B 17/28
[52] U.S. Cl. ................................. 128/340; 128/321
[58] Field of Search ............... 128/326, 325, 334 R, 128/340, 303 R, 321; 112/169, 80; 223/104

[56] References Cited

U.S. PATENT DOCUMENTS

| 662,178 | 11/1900 | Truax | 128/340 |
|---|---|---|---|
| 1,108,737 | 8/1914 | Gajdos | 128/340 |
| 2,327,353 | 8/1943 | Karle | 128/340 |
| 2,652,832 | 9/1953 | Castroviejo | 128/340 |
| 2,737,954 | 3/1956 | Knapp | 128/340 |
| 3,090,386 | 5/1963 | Curtis | 128/334 R |
| 3,638,654 | 2/1972 | Akuba | 128/340 |
| 4,235,177 | 11/1980 | Arbuckle | 128/334 R |

Primary Examiner—C. Fred Rosenbaum
Assistant Examiner—C. W. Shedd
Attorney, Agent, or Firm—Israel Nissenbaum

[57] ABSTRACT

A surgical needle holder for curved needles, comprised of movable gripping jaws offset from a manipulating handle thereof by a distance substantially equal to the radius of curvature of the specific needle to be held thereby. The gripping jaws are positioned relative to said handle such that the curved needle, held therebetween, is rotated only through its own curvature about an axis coincident with the axis of rotation of said handle. The manipulating handle is preferably comprised of at least one section thereof having a substantially circular cross section whereby said section may be manipulatively rolled between a surgeon's fingers to rotate said needle along its curvature during suturing. Tissue trauma and tearing during such suturing are substantially reduced thereby.

14 Claims, 3 Drawing Figures

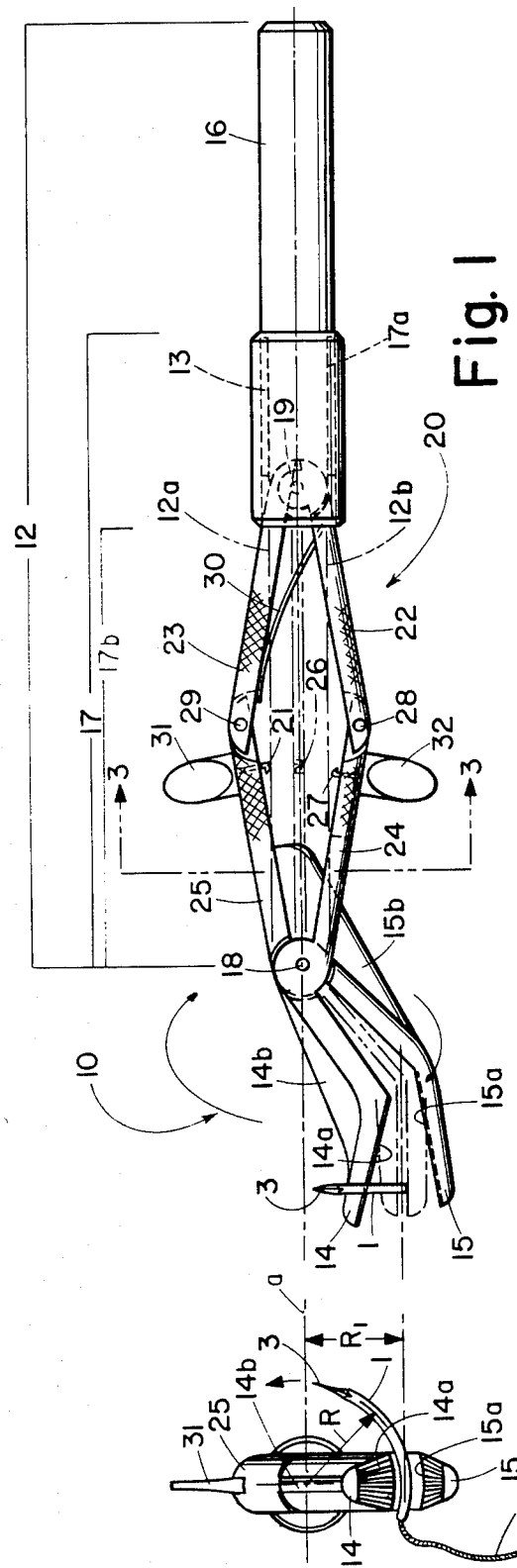
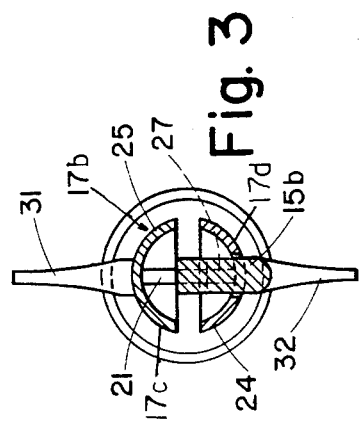

SURGICAL NEEDLE HOLDER

This invention relates to surgical needle holders and particularly to such holders for curved needles which holders are adapted for rapid one hand operation, engagement and disengagement with said needle during suturing.

Surgical needles are of two generally commercially available varieties; straight needles, and curved needles having a uniform radius of curvature with such needles either having surgical thread or suture swedged into the rear thereof or having eyelets for the inertion of such thread. For many situations the straight needles are preferred since they can be more easily handled. However, under some conditions, particularly those involving space restricted areas and delicate tissues, use of the curved needles is preferred. Such curved needles are however very difficult to properly manipulate manually and accordingly such needles are invariably utilized in conjunction with needle holders specially designed for use therewith. The most common of such needle holders comprises a device having a configuration somewhat like needle-nose pliers with clamping means for locking the gripping jaws thereof into a fixed position. Needle holders designed for use with needles used in delicate surgery such as eye surgery do not however require a clamping means since simple holding pressure during suturing is generally sufficient to prevent needle slippage.

Suturing with curved needles and the aforementioned needle holder is generally accomplished by engagement of the jaws of the needle holder with the needle at a point on the needle somewhere about the rear third thereof. The needle is then rotated, via the needle holder, by the hand, wrist and arm of the surgeon through an arc defined by the curvature of the needle into and partially through the tissues to be connected, with the needle having either a cutting or tapered point to facilitate such tissue perforation. While the needle is supported by the tissues, the needle holder is disengaged from the rear of the needle and is reengaged with the forward end of the needle which has already passed through the tissues. The stitch is then completed by pulling the remainder of the needle completely through and the thread partially through the tissues to be connected and tying the thread, or alternatively, particularly when connecting long sections of torn or lacerated tissues, continuing and suturing in accordance with the above procedure as required. During such procedure, manipulation of the needle holder should be a one hand operation in order to enable the surgeon to use a forceps to hold the tissues during suturing with the other hand.

During the above outlined procedure, unless the needle is constantly maintained in perfect alignment along it own curvature during suturing, there is a resistance being offered by the perforated tissues, with increased force being necessitated thereby, with resultant tissue trauma, with the formation of excessively large openings and possibly even tears in the tissue, and because they create a less than optimal suturing they all may retard proper healing. Furthermore, with excessive pressure and hard tissues, the needle itself may bend or break. With bent needles some surgeons may attempt to reshape the needle but invariably with a loss of true curvature, or even with detrimental kinks being formed in the needle. Proper manipulation of a curved needle and its holder during suturing to minimize such trauma and ill effects, is an acquired skill generally requiring from three to five years of practice to achieve a reliable wrist, hand and arm motion. Furthermore, even with such acquired skill, from long practice, some tissue trauma is inevitable because the suturing is still dependent upon a free arm motion without mechanical restraint. The following by the surgeon's hand of the needle's curvature becomes increasingly more difficult under conditions of obscured vision such as with excessive blood or long reaching, limited space, such as when reaching down into the abdomen or into the chest cavity in order to suture a heart valve or when working on very delicate tissues such as when suturing the cornea of an eye. In fact, the very reason for using a curved needle in the first place makes its proper use more difficult.

The necessity for maintaining movement of the curved needle along its curvature during suturing has been long recognized with various mechanical expedients for such maintenance having been disclosed. Such expedients, however, have generally been plagued with a variety of shortcomings in using them with proper suturing technique. For example, the surgical stitching instrument described in U.S. Pat. No. 2,737,954 utilizes a curved needle with an integral shank which passes through the center of the circle defined by the curvature of the needle. This shank is clamped at such point, in a relatively fixed manner, to a rotatable rod contained within a floating sleeve. Rotation of the rod in turn rotates the needle about its own curvature. However, such device embodies several severe disadvantages which are necessitated by its very mode of operation. Firstly, commercially available curved surgical needles cannot be used with such instrument since they generally have simple arc configurations without the integral shank for the holding thereof by the instrument. Secondly, the shank of the specially designed needle and its fixed clamping to the instrument causes, as described therein, the needle to be rotatable for only a fixed distance with retraction being required thereafter. Thus, the needle cannot be readily utilized for suturing procedures requiring more than one pass since the needle cannot be completely drawn through the tissues. Continuous stitching with such instrument would require tedious and time consuming threading and rethreading for any semblance of continuous operability. Finally, and even more disadvantageously, the aforementioned instrument requires two hands for manipulation thereof whereas, in suturing, it is highly desirable that one of the surgeon's hands be free for aiding the suturing process by using a forceps to grasp the tissue edges during suturing.

It is an object of the present invention to provide a holder for curved needles such as surgical needles which holder itself is capable of guiding a commercially available curved needle completely through tissues and only through a circle defined by the curvature of said needle without substantial deviation caused by free hand, wrist or arm motion.

It is a further object of the present invention to provide such needle holder wherein it is easily manipulated by one hand and is rapidly engageable and disengageable.

These and other objects, features and advantages of the present invention will become more evident from the following discussion as well as the drawings in which:

FIG. 1 is an elevation view of an embodiment of a needle holder of the present invention positioned for holding a curved needle;

FIG. 2 is a front end view of said needle holder in a position for engaging said curved needle; and FIG. 3 is a section view taken along line 3—3 of FIG. 1.

Generally the present invention comprises a holder adapted for manipulating a curved needle such as a surgical needle during sewing or suturing. The holder comprises a handle adapted for rotational manipulation thereof and means for securely holding a curved needle such as gripping jaws. Said holder further comprises means for effecting engagement and disengagement of said holding means with said needle with one hand manipulation. The holding means is adapted to hold said curved needle at a distance from the rotational axis of said handle to the point of said needle substantially equal to the radius of curvature (to the point thereof) of said needle. Said holding means further holds said curved needle in a position whereby rotation of said handle around its rotational axis moves the needle along a circle defined by the curvature of said needle. In a preferred embodiment of the present invention said holding means comprises gripping jaws with the holding surfaces thereof being offset from the rotational axis of said handle by a distance substantially equal to the radius of curvature of said needle to the point thereof. The gripping surfaces of the jaws of the needle holder are also generally parallel (with only slight deviation caused by the pitch of the jaws when engaged with the needle) to said rotational axis of said handle whereby the point of the curved needle held therebetween follows its own curvature in a circle around said rotational axis upon rotation of said handle. In order to effect such circular motion it is understood that the curved needle has an arc configuration with a uniform radius of curvature. In a further preferred embodiment, in order to facilitate rotational manipulation of the needle holder of the present invention, at least one portion or segment of the handle thereof has a circular cross section when the needle is being held in operative position. As a result, the handle, and concomitantly the needle holder and the needle, are rotated by simple rolling of such circular handle portion between the surgeon's fingers. Such rolling motion is essentially stable, particularly, since it obviates the need for any free hand, wrist or arm motion during suturing. To further ensure stability of such finger rolling whereby the needle follows only its own curvature, the handle of the needle holder further preferably comprises stationary as well as rotatable elements, with the stationary element being held in fixed position in the palm of the surgeon's hand and the last two or three fingers of the hand. Such stationary element may either be circular or may be preferably shaped to conform to the palm and fingers holding it. Thus, in such embodiment, while the rotational element is rolled by the surgeon's thumb and forefinger or thumb, forefinger and middle finger in performing suturing, the stationary element functions as a stabilized frame of reference therefor to ensure an essentially perfect circular motion of the needle.

Since the needle holder of the present invention obviates the need for hand, wrist or arm motion, little practice is required for the proper utilization thereof. Furthermore, the needle holder of the present invention provides an improved means for surgical stitching with substantial elimination of the previously inevitable tissue trauma and other associated problems of prior art devices.

The needle holder of the present invention is preferably specifically adapted to a single radius of curvature of the specific needle to be used therewith, with other needle holders of different radii of curvature being required for curved needles having correspondingly differing radii of curvature. Alternatively, the needle holder may be made adjustable for adaptation to such differing radii.

The gripping jaws of the needle holder preferably have carbided surfaces with cross hatchings to ensure a positive grip of the needle, and in a more preferred embodiment, the mating jaws are themselves curved (one concave and one convex) with a curvature which matches that of the needle. In such embodiment the needle automatically falls into an ideal position for perfect circular, rather than elliptical, motion during suturing. For finer suturing such as in eye surgery, the jaws may be left smooth but may either be straight or more preferably may be curved as described to match the curvature of the needle.

The gripping jaws are preferably affixed to the body of the needle holder and to each other by means of a pivot joint whereby they may be rapidly moved into surface engagement with one another to positively grip a needle or rapidly moved apart for disengagement from the needle as required. The joint may be a box type joint or simple hinge type joint or it may be a sliding type with a slot cut into one of the jaws to allow parallel action of the jaws relative to each other.

In a preferred embodiment, the rotatable element of the needle holder handle is also the controlling mechanism for effecting engagement and disengagement of the gripping jaws with the needle and is comprised of moveable joint elements. Such joint elements should have an external circular cross section when the needle is held by the jaws to facilitate the stabilized finger rotation described above. It is preferred that the needle holder further embody sequential latching means for fixing the moveable joint elements of the handle and which thereby clamp the gripping jaws into position in holding the needle. Such latching means should be readily operable with one hand. When the needle holder adapted for use with needles utilized in suturing of delicate tissue such as in eye surgery, such latching means is unnecessary since the pressure exerted by simply holding the needle holder is generally sufficient to maintain adequate gripping of the needle.

In an alternate embodiment, the controlling means for effecting engagement and disengagement of the gripping jaws are contained within the stationary element of the handle whereby movement of the rolling fingers may be further reduced. In such embodiment the jaws are connected to a solid rod or cable through which control movement such as by a squeezable pistol grip and spring loading, is effected for the engagement and disengagement of the gripping jaws. Other holding means such as a collet may be utilized in place of the gripping jaws with similar operable mechanisms for use in providing the requisite engagement and disengagement of the holding means with the curved needle.

In some instance, such as with an atherosclerotic placque, the simple rotation of the needle may be insufficient for initial needle perforation. Accordingly, the needle holder of the present invention may be further equipped with leverage means to increase the force exerted in the rotational mode. Such leverage means include tangs integrated with the rotational segment of the handle, with the tangs being turned by the thumb and forefinger of the surgeon's hand for additional turning power with concomitant perforation power, as required.

With particular reference to the drawings, FIGS. 1 and 2 depict a needle holder 10 in holding position (for a right handed surgeon) with a typical curved surgical needle 1 having a cutting point 3 for facilitated tissue perforation, a radius of curvature R (to the needle point) and a surgical thread 2 swedged into the rear end thereof. The needle holder 10 is specifically matched to needle 1 with the radius of curvature R of said needle (to the point thereof) being substantially equal to the distance $R_1$ between the rotational or longitudinal axis a of needle holder handle 12 and the position between gripping jaws 14 and 15 of said needle holder where the needle is held when said jaws are closed in engagement with said needle.

As a result of such specific offset positioning of the jaws 14 and 15 with respect to the axis of rotation of said handle 12, needle 1 held by said jaws, is rotated in a perfect circle defined by its own curvature, with rotation of handle 12 around axis a. To ensure such essentially perfect rotation, the cross section of segment 17b of handle 12 which is rotated is circular, as shown in FIG. 3 when the gripping jaws engage needle 1. Rotation of segment 17b is by the relatively stable rolling of such segment between the thumb and forefinger or between the thumb, forefinger and middle finger of the surgeon's hand. To facilitate such sure finger handling, semicylindrical section 17c and 17d have outer knurled surfaces. Further stability for such rotation is obtained by means of rear stationary segment 16 of handle 12 which is affixed to rotating forward segment 17 by means of bearing 13 which enables such relative rotation. Rear segment 16 is adapted to be fixedly cradled by the palm and last two or three fingers of the surgeon's hand for longitudinal stability during suturing by finger rotation of segment 17. Tangs 31 and 32 are utilized for exerting additional turning force on segment 17 when required.

Forward rotating segment 17 additionally provides the means for forcing the gripping jaws 14 and 15 into holding engagement and disengagement with a curved needle. Said handle segment 17 is comprised of a scissoring four bar (22,23,24 and 25) parallelogram 20 with bars 24 and 25 being directly connected with or integrated with jaws 14 and 15 respectively through pivot joint 18 to effect engaement and disengagement of said jaws by vertical movement of said bars. Bars 22 and 23 are attached to bars 24 and 25 respectively with toggle joints 28 and 29 respectively which are in turn affixed to section 17a of rotating segment 17 by pivot joint 19. Compression on the scissoring four bar parallelogram 20 by the fingers closes such bars into a substantially circular cross section configuration shown in FIG. 3, with jaws 14 and 15 being also thereby brought into position for gripping the needle.

Latching mechanism 26, comprised of engaging elements 21 and 27, clamps the bars 22,23,24 and 25 into the circular cross section configuration position as shown by the dotted lines. Latching mechanism 26 is sequential for rapid operation such that further compression of parallelogram 20 effects disengagement of engaging elements 21 and 27, opening of said parallelogram (assisted by leaf spring 30) and disengagement of jaws 14 and 15 from the needle when required.

The gripping surfaces 14a and 15a of jaws 14 and 15 are cross hatched and carbided to ensure positive engagement with the curved needle 1. As shown in FIGS. 1 and 2 jaws 14 and 15 have nesting convex and concave surfaces respectively with the curvature of such surfaces being substantially the same as that of needle 1. As a result, engagement of jaws 14 and 15 with needle 1 also effects proper alignment for circular rather than elliptical movement by the needle during suturing. With such configuration of the jaws' surfaces the needle is caused to automatically right itself thereby aligning the needle's radial axis with the axis of mutual perpendicularity of the jaws and the handle. The areas 14b and 15b resulting from the offset of jaws 14 and 15 from axis a are filled in to form a taper towards the tip of the jaws. This maintains a smooth snag free configuration of the jaw area adjacent the surgical thread during suturing, particularly since it is a common practice to wind such thread about the jaws of a needle holder to facilitate tying of the suture thread.

It is understood that the above description and the drawings of a particular embodiemnt of the present invention are illustrative in nature and that changes may be made to the structural elements and their arrangement without departing from the scope of the present invention as defined in the following claims.

What is claimed is:

1. A needle holder for one handed operative manipulation of a curved needle having a uniform radius of curvature, said needle holder comprising two jaws having engageable surfaces, for holding said needle therebetween and a manually manipulable handle characterized in that said handle comprises a rotatable element which is rotatable, by finger rotation, about an axis of rotation, with said surfaces being substantially parallel to said axis of rotation and wherein said jaws hold said needle at a distance, from said axis to the point of said needle, substantially equal to the radius of curvature of said needle to the point thereof and whereby said jaws hold said needle in a position whereby rotation of said handle element about said axis rotates said needle and the point thereof through a circle defined by the curvature of said needle and wherein said handle comprises a stationary element with one end being adapted to be held by the palm of said hand for stability and the other end thereof being rotatably connected by connecting means to said rotatable element, said holder further comprising means for permitting rapid one hand engagement and disengagement of said needle holder with said needle.

2. The needle holder of claim 1 wherein said engageable surfaces are matingly concave and convex with a curvature substantially matched to the curvature of said needle.

3. The needle holder of claim 1 wherein said means for engagement and disengagement comprises a scissoring four bar parallelogram with two of said bars being attached to said jaws through a pivot joint, whereby closure of said parallelogram effects engagement and the opening of said parallelogram effects disengagement of said jaws with said needle.

4. The needle holder of claim 3 wherein said four bar parallelogram comprises said rotatable handle element.

5. The needle holder of claim 1 wherein said stationary handle element comprises said means for permitting rapid one hand engagement and disengagement of said holding means with said needle.

6. The needle holder of claim 1 wherein said rotatable handle element has a circular cross section.

7. The needle holder of claim 6 wherein said rotatable handle element comprises a knurled outer surface.

8. The needle holder of claim 1 wherein said holder further embodies sequential latching elements which lock and unlock said holding means during engagement and disengagement respectively of said holder with said needle.

9. The needle holder of claim 1 wherein said rotatable handle element embodies leverage means for permitting an increase in power exerted for rotation.

10. The needle holder of claim 1 wherein said jaws are offset from said axis of rotation and wherein the area adjacent the outer portion of said jaws is filled in to provide a smooth tapered surface to the ends of said jaws.

11. The needle holder of claim 1 wherein said rotatable and stationary elements of said handle have a bearing surface therebetween.

12. A needle holder for one handed operative manipulation of a curved surgical needle having an arc shape with a uniform radius of curvature, said needle holder comprising engageable jaws having mating surfaces, said jaws being attached to a rotatable handle element, at one end thereof through a pivot joint characterized in that said rotatable handle element rotates about an axis substantially parallel to the mating surfaces of said jaws with said jaws being offset from said axis by a distance substantially equal to said radius of curvature of said curved needle whereby when said needle is held between said mating surfaces it is rotated through a circle defined by its own curvature with rotation of said rotatable handle element, said rotatable handle element comprising a scissoring four bar parallelogram having two of said bars attached to said jaws through said pivot joint wherein closure of said parallelogram causes mating engagement of said jaws with a needle held therebetween, said rotatable handle element being rotatably attached, at another end thereof opposite said jaws, with a bearing surface to a second handle element adapted to be held in stationary position in the palm of a hand during rotation of said rotatable handle element with said rotation of said rotatable handle element being effected by rolling thereof between the fingers of said hand and wherein said needle, held between said jaws, is rotated in a stable manner through substantially only its own radius of curvature.

13. The needle holder of claim 12 wherein said rotatable handle element is circular in cross section, when said jaws are engaged with said needle, and having a knurled outer surface.

14. The needle holder of claim 13 wherein said rotatable handle element further comprises sequential latching means which lock and unlock said jaws from engagement with said needle during engagement and disengagement respectively of said jaws with said needle.

* * * * *